US007203322B1

(12) United States Patent
Bostock

(10) Patent No.: US 7,203,322 B1
(45) Date of Patent: Apr. 10, 2007

(54) ACOUSTIC DETECTOR WITH NOISE CANCELLATION

(75) Inventor: Peter Bostock, Atherton, CA (US)

(73) Assignee: Metrotech Corporation, Santa Clara, CA (US)

( * ) Notice: Subject to any disclaimer, the term of this patent is extended or adjusted under 35 U.S.C. 154(b) by 669 days.

(21) Appl. No.: 10/440,353

(22) Filed: May 16, 2003

(51) Int. Cl.
*A61B 7/04* (2006.01)

(52) U.S. Cl. .......................... 381/67; 73/40.5 R; 73/40

(58) Field of Classification Search .................. 381/67, 381/94.7; 181/131; 600/528; 73/40.5 R, 73/40
See application file for complete search history.

(56) References Cited

U.S. PATENT DOCUMENTS 4,455,675 A 6/1984 Bose et al.
4,455,677 A * 6/1984 Fox ............................ 381/110
4,494,074 A 1/1985 Bose
5,610,987 A * 3/1997 Harley ........................ 381/67
5,744,700 A * 4/1998 Carme et al. ............ 73/40.5 A
5,952,618 A * 9/1999 Deslauriers ................. 181/131
6,163,504 A * 12/2000 Komninos et al. .......... 367/135
6,725,705 B1 * 4/2004 Huebler et al. .......... 73/40.5 A

OTHER PUBLICATIONS

"Model HL 400 Electroacoustic Leak Locator," Operation Manual, Metrotech, Jun. 1999.
"Noise Reduction Headphones," GoodCans.com retrieved on Jul. 16, 2001, from http://listeningstation.safeshopper.com/14/cat14.htm?395.
"HDC451-1 Active Noise Cancellation Portable Headphone," Sennheiser Electronic Corporation.

* cited by examiner

*Primary Examiner*—Brian T. Pendleton
(74) *Attorney, Agent, or Firm*—Finnegan, Henderson, Farabow, Garrett & Dunner, L.L.P.

(57) ABSTRACT

An acoustic detector that includes active noise cancellation is presented. An acoustic detector converts sound waves, which include sound waves of interest as well as noise, to an electronic signal. An operator listens for a characteristic sound, for example the sound characteristic of fluid leaking from a pipe, as she varies the position of the transducer. At least one other acoustic detector is positioned in order to monitor noise. The electronic signal from the noise monitoring acoustic detector and the electronic signal from the acoustic detector are combined in a processor in order to cancel the noise. In some embodiments, the operator may adjust a cancellation band so that some frequencies are not cancelled. For example, the operator may adjust the cancellation band so that a co-worker's voice may be heard.

27 Claims, 3 Drawing Sheets

ACOUSTIC DETECTOR WITH NOISE CANCELLATION

BACKGROUND

1. Field of the Invention

The invention relates to the field of acoustic detectors, and in particular, to leak detection equipment with active noise cancellation.

2. Related Art

When water or other fluids leak from underground pipes, quick and accurate determination of the site of the leak is necessary to reduce the amount of damage caused by leaking fluid. Acoustic sensing methods are used to locate leaks in underground pipes by detecting the vibrations caused by leaking fluids. Fluids leaking from underground pipes under pressure typically produce acoustic vibrations with a frequency in the range of about 40 Hz to about 4000 Hz.

In order to detect the acoustic vibrations, a transducer placed in contact with the ground converts the mechanical vibration into an electrical signal. The electrical signal is filtered to block most noise at frequencies below about 400 Hz and above about 2000 Hz. The signal can also be amplified before and/or after filtering. In some detectors, individual band-gap filters can be selected in order that ranges of frequencies can be monitored. The range of frequencies being monitored depends on the nature of the pipe, the material leaking from the pipe, the size of the leak, and the characteristics of the earth in which the pipe is buried.

The processed electrical signal can then be input to one or more speakers in a set of headphones, where it is converted back into acoustic vibrations. An operator wearing the headphones listens for the characteristic tone of the leak. The position of the transducer on the ground is varied in order to find the source of the leak. The operator must be able to accurately determine the spot at which the characteristic tone has a maximum volume in order that an accurate location of the leak is determined.

During leak detection, the sound reaching the operator's ear is primarily a combination of the sound attributable to the leak, noise picked up by the transducer and passed through the electronics to the headphones, and ambient noise transmitted through the air and through the headphone structure. An operator's ability to locate sound precisely depends in part on how well the sound of the leak can be distinguished over other sounds.

Ambient noise protection headphones, which are commonly utilized to reduce ambient background noise, have several disadvantages. First, the attenuation efficiency is limited by the quality of the seal to the operator's ears and by the characteristics of the foam cushions. Therefore, ambient noise protection headphones may not attenuate noise sufficiently to allow an operator to accurately determine the source of the leak. Second, the attenuation is indiscriminate. Sounds that the operator may need to hear, such as the sound of a co-worker's yelling a warning, are attenuated along with the unwanted background noise. Therefore, ambient noise protection headphones may pose a safety risk to the operator.

Active Noise Cancellation (ANC) headphones, which cancel unwanted noise instead of merely attenuating it, provide a better solution. ANC headphones contain microphones that convert environmental noise to an electrical signal that can then be utilized to produce sound of equal amplitude but opposite phase of the ambient noise. The signal from the leak detector, as with a CD or DVD player, can be input and the operator can monitor the sound produced by the leak detector while canceling ambient noise at the headphones.

ANC headphones are marketed by, for example, Bose Corporation of Framingham, MA, Sony Corporation of Tokyo, Japan, and Sennheiser Electronic Corporation of Old Lyme, CT. However, existing ANC headphones are not designed to operate effectively in the frequency spectrum of interest for detecting leaks, e.g. about 40 Hz to about 4000 Hz. For example, the Sony MDR-NC5 has active noise cancellation that operates to a maximum frequency of 1500 Hz, but has a 15 dB noise cancellation only at frequencies less than 300 Hz. The Sennheiser HDC451-1 has 10 dB noise reduction between 400 Hz, and has maximum operating frequency of 1000 Hz. Additionally, these noise cancellation headphones do not cancel noise detected by the acoustic detector of the leak detector. Also, providing noise cancellation for all noise in the spectrum may present a safety hazard to the operator, who then can not hear warning shouts or traffic noise.

Therefore, in order to increase operator safety and accuracy, an acoustic leak detection system with active noise cancellation is desired.

SUMMARY OF THE INVENTION

In accordance with the present invention, an acoustic leak detector with active noise cancellation is presented. An acoustic leak detector includes an acoustic sensor to convert acoustic waves to electronic signals. The acoustic sensor is then utilized to detect leak noises from an underground pipe. In some embodiments, a second acoustic sensor is provided to monitor background noise and provide an electronic signal that cancels the noise from the electronic signal provided by the acoustic sensor. In some embodiments, the second acoustic sensor can be placed in contact with the earth away from the pipe in order to cancel noise that is transmitted from surrounding sources through the earth. In some embodiments, the second acoustic sensor monitor can be placed such as to detect noise in air in the vicinity of the acoustic leak detector.

In some embodiments, the acoustic leak detector can further include active noise cancellation at the headset. The active noise cancellation at the headset can be frequency dependent so that certain sounds, for example traffic noise, can be monitored by the operator.

In some embodiments, an acoustic leak detector according to the present invention can include several noise cancellation systems. For example, the acoustic leak detector can include a noise cancellation system with a first acoustic detector positioned on the earth away from the pipe in order to cancel noise that is transmitted through the earth, a noise cancellation system with an acoustic detector positioned close to the acoustic detector in order to cancel ambient background noise at the acoustic detector; and an acoustic detector located in the headphones to selectively cancel ambient noise in the headphones.

The acoustic sensors may be of any device for detecting sound waves, such as piezoelectric transducers, microphones, or other acoustic sensors. The electronic signals output by the acoustic sensors are input to an electronic processing module. The electronic processing module amplifies and filters the signals detected from the acoustic sensors and combines the signals from the acoustic detectors to reduce the acoustic noise heard by the operator, making the sound produced by the leak more easily discernable.

In some embodiments, the headphones have two insulated shells which are held snugly to an operator's head by a headband. Each shell includes a microphone, which detects acoustic waves and converts them to an electronic signal. This electronic signal, along with the modified electronic signal from the electronic processing module that corresponds to the acoustic waves of interest, are input to the processor. The processor compares the electronic signals from the microphones to the modified electronic signal from the processing module and produces a cancellation signal. The cancellation signal is opposite in phase and of the same magnitude as the portion of the electronic signal from the speaker of the ANC headphones attributable to noise rather than the signal of interest. In some embodiments, the operator can mute the signal of interest and enhance the signal from the microphones in order to better hear the ambient noise signal which would have been cancelled.

In some embodiments, the electronic signal from the microphone in the headphones can be processed through a filter. Some of the noise measured by the microphone in the headphones, then, is not canceled. For example, the noise cancellation system may include an adjustable filter, letting the operator choose a frequency band that will not be cancelled by the processor. Alternately, the operator may choose to cancel only a specific frequency band. For example, to increase operator safety during acoustic detection, the operator may choose to cancel only those frequencies close to the frequency band of interest, so that noise outside this band is not cancelled but merely attenuated by the insulation of the headphone shells. The operator may also choose to allow sounds within selected bands of frequencies to not be cancelled. Alternately, the cancellation band may be set automatically or by a person other than the operator; for example, the acoustic detection system may be calibrated prior to use.

According to some embodiments of the invention, the acoustic sensors can be transducers such as piezoelectric transducers. The transducer utilized to measure the leak noise can be mounted on a support, which holds the transducer so that it is acoustically coupled to the surface of the ground. The electronic processing module may be mounted to the support, or may be carried by the operator; for example, it may be carried from a shoulder handle. The operator wears the headphones, which are connected to the electronic processing module. In some embodiments, the headphones can also provide some active noise cancellation.

According to some embodiments of the invention, an acoustic detector includes an acoustic sensor such as a transducer, and an acoustic barrier to shield the transducer from ambient noise transmitted through air. The acoustic detector may also include active noise cancellation circuitry to cancel noise inside the acoustic barrier.

According to some embodiments of the invention, an operator may use the embodiments of acoustic detection systems described above to find the position of a water leak in an underground pipe. The operator places the transducer so that it is acoustically coupled to the surface and listens for leak sounds. The operator may adjust the operating parameters of one or more noise cancellation systems. For example, the cancellation frequency band may be adjusted to optimize the operator's ability to detect leak sounds while maintaining a level of safety for the operator.

A more complete understanding of embodiments of the present invention will be appreciated by those skilled in the art, as well as a realization of additional advantages thereof, by a consideration of the following detailed description of one or more embodiments. Reference will be made to the appended drawing that will first be described briefly.

BRIEF DESCRIPTION OF THE DRAWING

Use of the same or similar reference numbers in different figures indicates the same or like elements.

DETAILED DESCRIPTION

Figure 1:
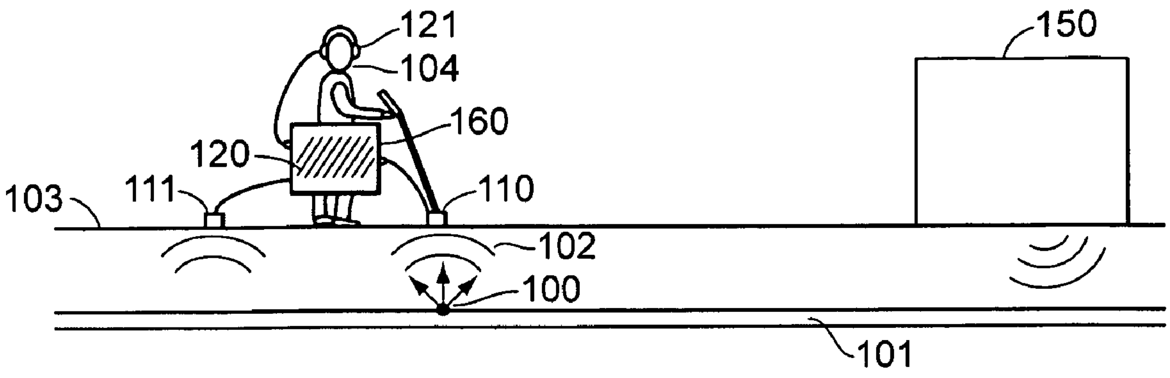
FIG. 1 shows operation of an acoustic leak detector according to the present invention in the presence of noise producing equipment.

FIG. 1 shows a schematic diagram of an acoustic detection system, according to an embodiment of the invention. An acoustic detection system 160 of FIG. 1 shows a system for detecting the position of a leak 100 in an underground pipe 101. in some embodiments, acoustic detection systems according to the invention may be used for other purposes, such as, for example, to detect the position of a buried pipe where mechanical vibrations applied to an exposed portion of pipe may be detected above an underground portion.

A leak 100 in a pipe 101 emits leak sounds 102. The frequency of leak sounds 102 generally lies in a frequency range between $\upsilon_{min}$ of approximately 40 Hz and $\upsilon_{max}$ of approximately 4000 Hz, although specific leaks in specific pipes (e.g., water leaks in water lines) may emit leak sounds in much more narrow frequency ranges. The frequency range of acoustic waves produced by other systems may lie in a different frequency range with a different $\upsilon_{min}$ and $\upsilon_{max}$.

An acoustic detector 110 converts leak sounds 102, as well as noise picked up by acoustic detector 110, into an electronic signal, which is coupled into processing unit 120. Acoustic detector 110 may, for example, be a piezoelectric transducer, a microphone, or other acoustic detector capable of converting acoustic waves to electronic signals. A second acoustic detector 111 can be placed away from leak 100 to monitor background noise. In some embodiments, as shown in FIG. 1, acoustic detector 111 can be placed in contact with ground 103, as is acoustic detector 110, in order to detect noise transmitted through ground 103. In some embodiments, acoustic detector 111 can be placed on or around processor 120 in order to detect noise. Acoustic detector 111, as is acoustic detector 110, can be any device which converts acoustic waves to electrical signals, for example piezoelectric transducers, microphones, or any other device capable of converting acoustic waves to electronic signals. In some embodiments, multiple acoustic detectors may be placed around acoustic detector 110 to provide electrical signals for noise cancellation in processor 120.

Noise generator 150 shown in FIG. 1 depicts any noise producing device. For example, generator 150 can be heavy equipment (e.g., backhoes, bulldozers, trucks, etc.), can be permanently installed units such as pumps or air conditioners, or can be such devices as jackhammers. Noise produced by generator 150 can be coupled into earth 103 or transmitted through air and degrades the ability of operator 104 to detect leak noise 102.

Processing unit 120 processes the electrical signals from acoustic detectors 110 and 111 to produce a signal which can be reconverted into an acoustic signal at earphones 121. Operator 104 monitors the acoustic signal at earphones 121 in order to detect leak sounds 102 from pipe 101.

Figure 2:
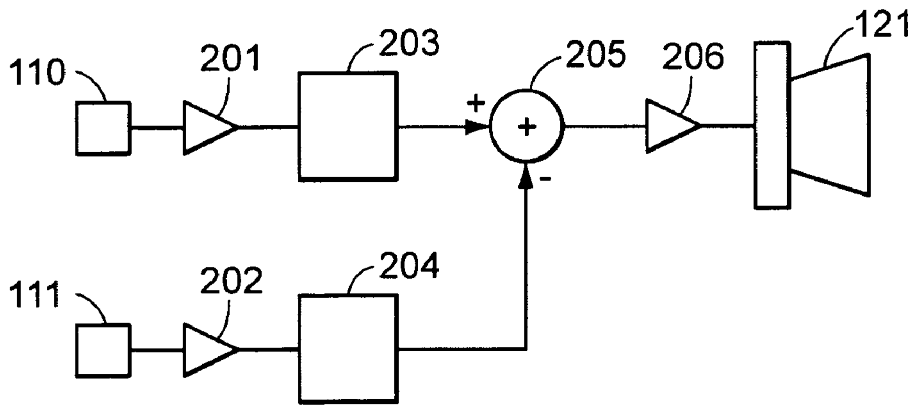
FIG. 2 shows a block diagram of an embodiment of a noise cancellation circuit according to the present invention.

FIG. 2 shows an example block diagram of a signal processing circuit of processor 120. The electrical signal from acoustic detector 110 is received in an amplifier 201. In some embodiments, the gain of amplifier 201 can be controlled by operator 104. In some embodiments, the gain of amplifier 201 can be preset. The output signal from amplifier 201 can be input to a filter 203. Filter 203 can be a band-gap filter set to one of a set of preselected bands, which can be operator selected or may be pre-determined. In some embodiments, filter 203 can be set to pass only signals in a narrow band corresponding to leak sounds of a particular type of leak.

The electrical signal from acoustic detector 111 is input to amplifier 202. The gain of amplifier 202, in some embodiments, can be operator selected. In some embodiments, the gain of amplifier 202 can be preselected. In some embodiments, the gain of amplifier 202 can be selected to be the gain of amplifier 201 plus a user-selected gain. The output signal from amplifier 202 is input to filter 204. Filter 204 can be set to pass signals within one of a preselected set of bands or may be fixed. In some embodiments, external noise within a certain band can be passed so that the operator can monitor certain background noises, for example, surrounding traffic.

The output signal from filter 204 is subtracted from the output signal from filter 203 in summer 205. In some embodiments, the output signal from summer 205 is input to amplifier 206. In some embodiments of the invention, filtering may occur after summer 205. In other words, filter 203 may be positioned after summer 205. In some embodiments of the invention, certain bands of frequencies in the signal received from acoustic detector 111 are not cancelled.

Amplifier 206 can have a user-controlled gain, which is utilized to select the volume of sound produced by headphones 121. In some embodiments, headphones 121 can be a standard set of headphones or earphones. In some embodiments of the invention, processor 120 can include a microprocessor and processing of signals (including filtering and noise cancellation) can be accomplished digitally.

Figure 3A:
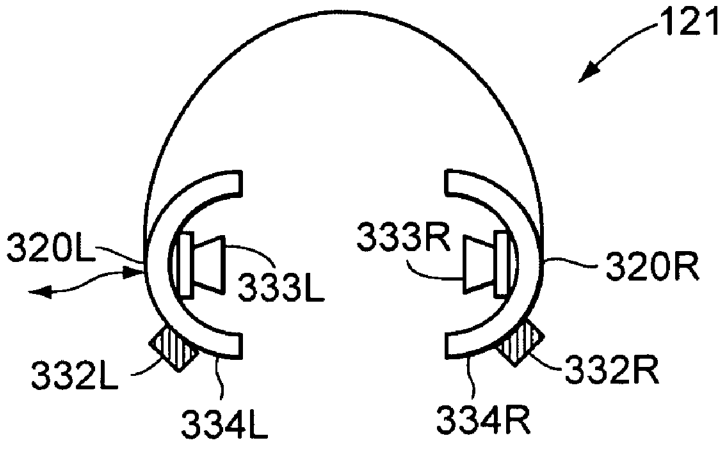
FIG. 3A shows a diagram for active noise cancellation headphones of an embodiment of an acoustic leak detector according to the present invention.

According to some embodiments of the invention, headphones 121 can include active noise cancellation to further improve the measurement process. As shown in FIG. 3A, headphones 121 can include two insulated shells 320L and 320R, which may be semi-hemispherical. Insulation 334L and 334R attenuates environmental noise, although some noise passes through the insulation. In embodiments with active noise cancellation, microphone 332L and 332R convert ambient sound waves at shells 320L and 320R, respectively, to electronic signals. The electrical signals produced by microphones 332L and 332R include both ambient environmental noise and attenuated leak sounds provided to the interior of shells 320L and 320R, respectively, through speakers 333L and 333R, respectively.

Figure 3B:
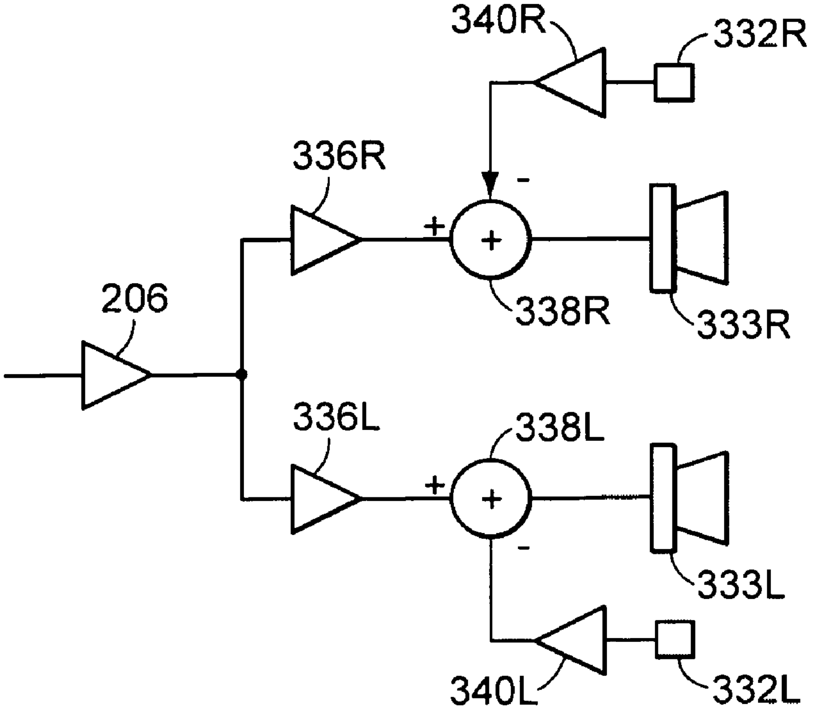
FIGS. 3B and 3C show block diagrams of active noise cancellation circuits for canceling noise at the headphones shown in FIG. 3A.

As shown in FIG. 3B, a portion of the electrical signals from microphones 332R and 332L can be subtracted from the signal provided to speakers 332R and 332L, respectively, to cancel the ambient noise. In the block diagram shown in FIG. 3B, the signal from amplifier 206 (see FIG. 2) is split into left (L) and right (R) channels. Each channel differentiates between the portion of the signal from speakers 332R and 332L that is due to ambient noise and which is leak noise (i.e., the output signal from amplifier 206) and produces an electrical signal which includes the leak noise and which will cancel the ambient noise. Ambient noise is cancelled by producing sound at speakers 333L and 333R that has the same amplitude and opposite phase from the ambient noise.

The output signal from amplifier 206, as shown in FIG. 3B, is summed in summer 338R with the inverse of the signal from microphone 332R. Amplifier 336R amplifies the output signal from amplifier 206 by substantially two (2). Amplifier 340R amplifies the output signal from microphone 332R such that the leak signal has an intensity approximately that of the output signal from amplifier 206. In some embodiments, the gains of amplifiers 336R and 340R can be user adjusted to maximize performance. In some embodiments, the gains may be fixed. The output signal from summer 338R, then, is the leak signal output from amplifier plus a signal corresponding to the inverse of the noise signal. The inverse noise signal, then, will cancel the noise in shell 320R. The left channel, which includes amplifiers 336L and 340L as well as summer 338L, operates identically as described above with regard to the right channel.

By using active noise cancellation at headphones 121 instead of increasing the noise attenuation (by thickening insulation 134 or increasing the force with which headphones 130 are held to the operators head), unwanted noise is eliminated more efficiently. Furthermore, the noise cancellation characteristics of acoustic detection system 160 may be varied to prevent noise cancellation of sounds that the operator may need to hear.

Figure 3C:
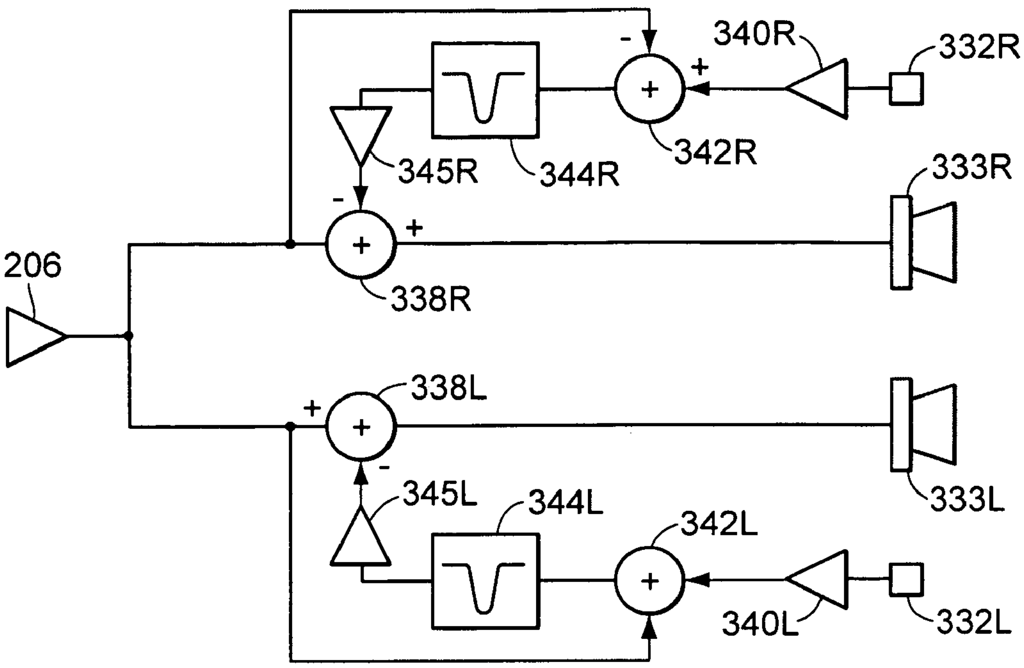

FIG. 3C shows an embodiment of an active noise cancellation circuit which can selectively cancel noise in headphones 121. Instead of, in effect, subtracting the signal output by microphone 332R from a multiple of the signal output from amplifier 206 to form a signal with the output from amplifier 206 plus an inverse of signal due to noise, the noise signal is isolated in summer 342R and filtered in filter 344R before being subtracted from the output signal from amplifier 206 in summer 338R. Filter 344R can be a stop band filter which passes all frequencies except those in the band that operator 104 needs to hear, for example shouts from colleagues or traffic noise. In some embodiments, operator 104 can select the characteristics of filter 344R to optimize the ability to safely detect leaks. Additional amplifiers can be provided to adjust the amount of cancellation at summers 338R and 338L. In FIG. 3C, amplifiers 345R and 345L are shown, but one skilled in the art will recognize that other parts of the circuit shown in FIG. 3C may also include amplification.

In some embodiments, the operator may adjust the magnitude of cancellation using a noise cancellation magnitude control, thereby decreasing but not eliminating residual environmental noise. The noise cancellation magnitude control can adjust the gain of amplifiers 340R, 340L, 345R, 345L and any other amplifiers as well as the proportion of the output signal from amplifier 206 that is subtracted in summer 342R and 342L. Additionally, in some embodiments, the operator may adjust the cancellation band by controlling the characteristics of filter 344R and 344L to allow important background noise to be heard through headphones 130. For example, the operator may adjust the cancellation band to cancel signals in the frequency range of interest, while background noise at other frequencies is merely attenuated by insulation 134. In such a case, a sound such as a warning shout of a co-worker would not be cancelled by the noise cancellation circuitry but merely be attenuated by insulation 134. In some embodiments, the operator may actually enhance the ambient signal in the frequency range of interest in order to hear some background noise better.

Figure 4:
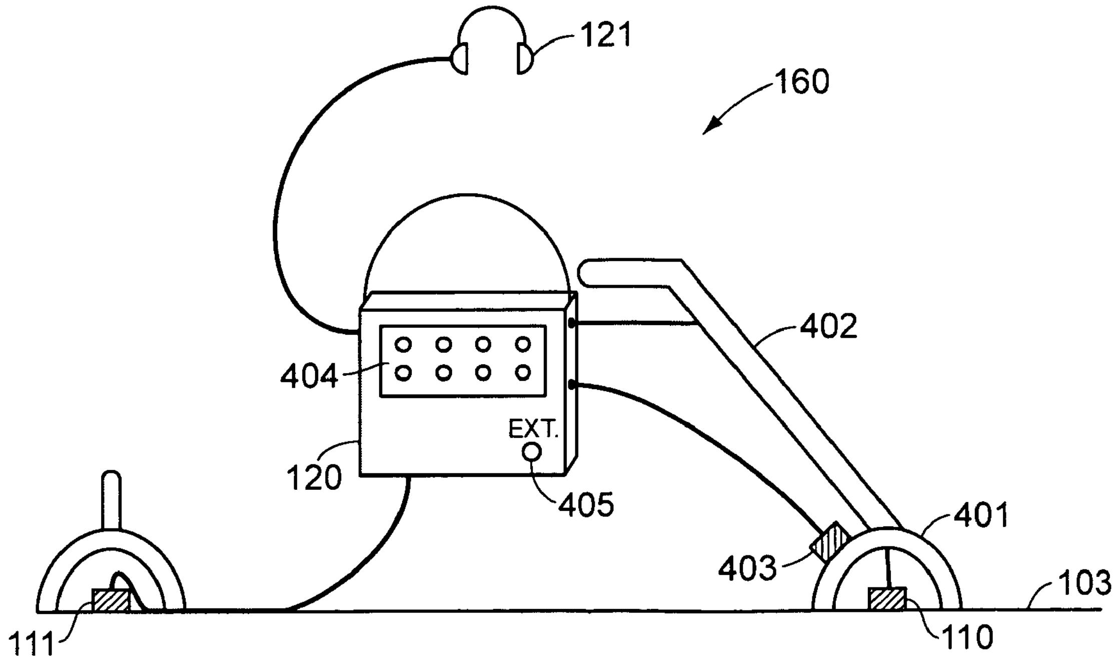
FIG. 4 shows an embodiment of an acoustic leak detector according to the present invention with multiple active noise cancellation systems.

FIG. 4 shows an embodiment of leak detector 160 with several active noise cancellation components. As discussed above, headphones 121 may be active noise cancellation headphones. Further, acoustic detector 111 can provide a noise signal to cancel noise from the signal of acoustic detector 110 that is transmitted through ground 103. The embodiment of acoustic detector 110 shown in FIG. 4 can be housed in a sound insulating dome 401 that can be mounted on a carrying handle 402. Sound insulating acoustic barrier 401, when placed flat on earth 103, contacting acoustic detector 110 with the surface of earth 103, can attenuate some external ambient noise transmitted through air.

Acoustic barrier 401 is positioned to attenuate noise but to not attenuate the acoustic waves of interest. Acoustic barrier 401 may be semi-hemispherical, so that acoustic detector 110 is placed in acoustic contact with a surface 103, the acoustic barrier blocks noise from above surface 103. At least a portion of acoustic barrier 401 may be flexible rather than rigid, so that upon pressure, the lower surface of acoustic 401 barrier conforms to the contours of surface 103 for more effective noise attenuation.

In some embodiments, an external acoustic detector 403, provided in the vicinity of or on dome 401, can provide a signal for canceling ambient noise. In some embodiments, signals related to ambient noise as well as signals from acoustic waves travelling through earth 103, are provided by acoustic detector 111. In some embodiments, acoustic detector 111 can be mounted in a second domed acoustic barrier 406, which is similar to dome 401. Although acoustic barrier 401 attenuates ambient noise, it does not remove it completely. In the region near surface 103, the ambient noise may include an appreciable component in or near the frequency range of interest which will not be filtered out as the signal from the detector passes through the amplification and filter stage.

Separate operator controls for controlling parameters of the noise cancellation, for example filter characteristics or amplifier gains, can be located anywhere on leak detector 160, including on the earphones or on processing unit 120. As shown in FIG. 4, controls 404 are mounted on processor 120. Controls 404 provide individual controls to individual noise cancellation circuits and to provide input controls for those circuits. In some embodiments, an external interface 405 on processing unit 120 can include a communication line. A signal from the communication line at interface 405 can be mixed into the signal acoustic detectors 110 so that operator 104 can communicate with co-workers or receive emergency warnings or instructions without removing or switching off noise cancellation.

In some embodiments, microphone 111 can be a contact microphone. A contact microphone typically includes a piezo-electric modulator mounted on a metal rod. The tip of the metal rod can be brought in contact with, for example, a hydrant or other structure to monitor ambient noise.

The embodiments described above are exemplary only and are not intended to be limiting. One skilled in the art may recognize various possible modifications that are intended to be within the spirit and scope of this disclosure. As such, the invention is limited only by the following claims.

I claim:

1. An acoustic leak detector, comprising:
an acoustic sensor to provide an electronic signal in response to acoustic waves;
at least one noise monitoring acoustic sensor placed proximate to the acoustic sensor, each of the at least one noise monitoring acoustic sensors providing a noise signal in response to ambient noise;
a processor coupled to receive the electronic signal and noise signals from each of the at least one noise monitoring acoustic sensors, the processor including a processing circuit that combines the noise signals and the electronic signal to form a noise cancelled signal and that allows cancellation of noise with a selected band of frequencies being selectable by a user,
wherein the noise cancelled signal includes a leak signal if a leak is detected.

2. An acoustic leak detector, comprising:
an acoustic sensor to provide an electronic signal in response to acoustic waves;
at least one noise monitoring acoustic sensor placed proximate to the acoustic sensor, each of the at least one noise monitoring acoustic sensors providing a noise signal in response to ambient noise;
a processor coupled to receive the electronic signal and noise signals from each of the at least one noise monitoring acoustic sensors, the processor including a processing circuit that combines the noise signals and the electronic signal to form a noise cancelled signal;
control inputs operable by a user that control parameters in the processing system that determine how the noise signal from each of the at least one noise monitoring acoustic sensors is combined with the electronic signal,
wherein the noise cancelled signal includes a leak signal if a leak is detected.

3. The detector of claim 2, wherein the parameters include amplifier gains.

4. The detector of claim 2, wherein the parameters include filter parameters for choosing selected bands of frequency in which noise is to be cancelled.

5. The detector of claim 1, wherein at least one of the noise monitoring acoustic sensors is an earth monitoring acoustic detector that can be positioned similar to but away from the acoustic sensor.

6. The detector of claim 5, wherein the noise signal from the earth monitoring acoustic sensor is filtered and then subtracted from the electronic signal.

7. The detector of claim 6, wherein the noise signal is filtered such that noise is cancelled in a band of frequencies.

8. The detector of claim 1, wherein at least one of the noise monitoring acoustic sensors is an ambient noise monitoring acoustic sensor that can be positioned proximate to the acoustic sensor.

9. The detector of claim 8, wherein the acoustic sensor is placed inside a sound deadening dome and the ambient noise monitoring acoustic sensor is placed proximate to the dome.

10. The detector of claim 9, wherein the ambient noise monitoring acoustic sensor is placed inside a separate dome that can be positioned at a distance from the sound deading dome.

11. The detector of claim 8, wherein a signal related to the noise signal from the ambient noise monitoring acoustic sensor is subtracted from the electronic signal.

12. The detector of claim 11, wherein the processing circuit includes a filter coupled to form the signal from the noise signal.

13. The detector of claim 11, wherein the processing circuit includes an amplifier coupled to form the signal from the noise signal.

14. The detector of claim 1, further including headphones to acoustically monitor the noise cancelled signal.

15. The detector of claim 14, wherein the headphones are active noise cancellation headphones.

16. The detector of claim 15, wherein the processing circuit adds a signal derived from signals from the noise cancellation headphones to the electronic signal to generate sound at speakers in the headphones which cancels the ambient noise for the user.

17. An acoustic leak detector, comprising:

an acoustic sensor to provide an electronic signal in response to acoustic waves;

at least one noise monitoring acoustic sensor placed proximate to the acoustic sensor, each of the at least one noise monitoring acoustic sensors providing a noise signal in response to ambient noise;

a processor coupled to receive the electronic signal and noise signals from each of the at least one noise monitoring acoustic sensors, the processor including a processing circuit that combines the noise signals and the electronic signal to form a noise cancelled signal;

headphones to acoustically monitor the noise cancelled signal, wherein the headphones are active noise cancellation headphones, wherein the processing circuit adds a signal derived from signals from the noise cancellation headphones to the electronic signal to generate sound at speakers in the headphones cancelling the ambient noise for the user and includes a filter which cancels noise detected by headphone acoustic couplers in a preselected band of frequencies, wherein the noise cancelled signal includes a leak signal if a leak is detected.

18. The detector of claim 17 wherein the preselected band of frequencies can be set by a user.

19. The detector of claim 1, wherein the processing unit further includes a terminal to receive an external communications signal, the external communications signal being combined with the electronic signal.

20. A method of detecting a leak, comprising:

measuring acoustic waves from the leak with an acoustic detector to provide an electronic signal;

measuring a noise signal at a location proximate the acoustic detector;

combining the noise signal with the electronic signal in order to produce a noise cancelled signal, wherein combining the noise signal includes filtering the noise signal with a selected band of frequencies being selectable by a user; and acoustically monitoring the noise cancelled signal to detect the leak.

21. The method of claim 20, wherein measuring acoustic waves includes positioning the acoustic detector to find the leak.

22. The method of claim 20, wherein measuring a noise signal includes positioning a second acoustic detector proximate the acoustic detector to monitor noise signals.

23. The method of claim 22, wherein positioning the second acoustic detector can include placing the second acoustic detector in contact with the earth away from the leak.

24. The method of claim 20, wherein combining the noise signal with the electronic signal can include amplifying the noise signal and subtracting the noise signal from the electronic signal.

25. The method of claim 20, wherein filtering the noise signal can result in cancellation of noise within a preselected band of frequencies.

26. The method of claim 24, further including removing the noise signal from the second acoustic detector.

27. The method of claim 22, wherein positioning a second acoustic detector to monitor a noise signal includes placing the second acoustic detector proximate to the acoustic detector that finds the leak.

* * * * *